United States Patent
Yan et al.

(10) Patent No.: US 10,217,201 B2
(45) Date of Patent: Feb. 26, 2019

(54) IMAGE PROCESSING METHOD, IMAGE PROCESSING SYSTEM, AND IMAGING SYSTEM

(71) Applicant: GENERAL ELECTRIC COMPANY, Schenectady, NY (US)

(72) Inventors: Ming Yan, ShangHai (CN); Kun Tao, ShangHai (CN); Dejun Wang, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 81 days.

(21) Appl. No.: 15/360,569

(22) Filed: Nov. 23, 2016

(65) Prior Publication Data

US 2017/0178303 A1   Jun. 22, 2017

(30) Foreign Application Priority Data

Dec. 17, 2015 (CN) .......................... 2015 1 0953747

(51) Int. Cl.
*G06K 9/00*  (2006.01)
*G06T 5/20*  (2006.01)
(Continued)

(52) U.S. Cl.
CPC ................. *G06T 5/20* (2013.01); *A61B 6/00* (2013.01); *G06T 5/002* (2013.01); *G06T 5/50* (2013.01);
(Continued)

(58) Field of Classification Search
CPC .. G06T 5/20; G06T 5/50; G06T 5/002; G06T 7/0012; G06T 7/0085; G06T 11/60; G06T 2207/10116; G06T 2207/20024; G06T 2207/20221; G06T 2207/20224; A61B 6/00
See application file for complete search history.

(56) References Cited

U.S. PATENT DOCUMENTS 7,471,320 B2  12/2008  Malkin et al.
8,582,855 B2  11/2013  Koehler
(Continued)

OTHER PUBLICATIONS

Zhang et al., "Metal Artifact Reduction in X-Ray Computed Tomography (Ct) by Constrained Optimization.", Med Phys, vol. 38, Issue 2, pp. 701-711, Feb. 2011.
(Continued)

*Primary Examiner* — Shefali D Goradia
(74) *Attorney, Agent, or Firm* — GE Global Patent Operation; Marc A. Vivenzio

(57) ABSTRACT

An image processing method comprises: identifying a weak edge comprising a plurality of weak edge pixels and a strong edge comprising a plurality of strong edge pixels in an input image; filtering at least a part of said input image to obtain a smoothed image, during which said weak edge in said input image is filtered with a first filter and said strong edge in said input image is filtered with a second filter having a smoothness less than that of said first filter; acquiring edge information of said input image based on said input image and said smoothed image; and generating an output image based on said edge information and said smoothed image. The present invention further relates to an image processing system and an imaging system.

10 Claims, 7 Drawing Sheets

(51) Int. Cl.
*A61B 6/00* (2006.01)
*G06T 5/00* (2006.01)
*G06T 5/50* (2006.01)
*G06T 7/00* (2017.01)
*G06T 11/60* (2006.01)

(52) U.S. Cl.
CPC .......... *G06T 7/0012* (2013.01); *G06T 7/0085* (2013.01); *G06T 11/60* (2013.01); *G06T 2207/10116* (2013.01); *G06T 2207/20024* (2013.01); *G06T 2207/20221* (2013.01); *G06T 2207/20224* (2013.01)

(56) References Cited

U.S. PATENT DOCUMENTS

| | | | |
|---|---|---|---|
| 8,655,097 B2 * | 2/2014 | Chien | G06T 5/005 382/261 |
| 2006/0227928 A1 | 10/2006 | Timmer | |
| 2008/0219532 A1 | 9/2008 | Hopkins et al. | |
| 2011/0273621 A1* | 11/2011 | Richardson | H04N 21/4402 348/608 |
| 2013/0039556 A1 | 2/2013 | Kachelriess et al. | |
| 2013/0278829 A1* | 10/2013 | Tegzes | H04N 5/21 348/607 |
| 2014/0193086 A1 | 7/2014 | Zhang et al. | |

OTHER PUBLICATIONS

Bom et al., "Reduction of Coil Mass Artifacts in High-Resolution Flat Detector Conebeam CT of Cerebral Stent-Assisted Coiling", AJNR Am J Neuroradio, vol. 34, pp. 2163-2170, Nov. 2013.
Zhang et al., "A Hybrid Metal Artifact Reduction Algorithm for X-Ray CT.", Med Phys, vol. 40, Issue 4, 2013.
"1k2 digital imaging chain", Philips, http://www.healthcare.philips.com/main/products/xray/products/c_arms/bvvectra/features.wpd, 2015.

* cited by examiner

IMAGE PROCESSING METHOD, IMAGE PROCESSING SYSTEM, AND IMAGING SYSTEM

BACKGROUND

In a medical image processing field, edge enhancement will usually be performed on an original image such that more details can be displayed in the image, which help a doctor make more accurate diagnosis. However, when a stronger edge (e.g., an edge of metal and the like) exists in the original image, overshoot or undershoot artifacts will be left on the image after the edge enhancement. An artifact refers to an image appearing on the image outputted by a medical image device that does not conform with an actual anatomical structure. The appearance of the artifacts will greatly reduce quality of an output image, and sometimes even cause the image not to be used for diagnosis.

Therefore, it is necessary to provide a novel image processing method, image processing system and imaging system so as to solve the above-described problems.

BRIEF SUMMARY

In one aspect, an embodiment of the present invention relates to an image processing method, comprising: identifying a weak edge comprising a plurality of weak edge pixels and a strong edge comprising a plurality of strong edge pixels in an input image; filtering at least a part of said input image to obtain a smoothed image, during which said weak edge in said input image is filtered with a first filter and said strong edge in said input image is filtered with a second filter having a smoothness less than that of said first filter; acquiring edge information of said input image based on said input image and said smoothed image; and generating an output image based on said edge information and said smoothed image.

In another aspect, an embodiment of the present invention relates to an image processing system, comprising an edge identifying means, a filter, an edge information acquiring means and an image compositing means. Said edge identifying means is used for identifying a weak edge comprising a plurality of weak edge pixels and a strong edge comprising a plurality of strong edge pixels in an input image. Said filter is used for filtering at least a part of said input image to obtain a smoothed image. Said filter comprises a first filter and a second filter. During the filtering, said first filter is used for filtering said weak edge in said input image and said second filter is used for filtering said strong edge in said input image, a smoothness of said second filter being less than that of said first filter. Said edge information acquiring means is used for acquiring edge information of said input image based on said input image and said smoothed image. Said image compositing means is used for generating an output image based on said edge information and said smoothed image.

In yet another aspect, an embodiment of the present invention relates to an imaging system, comprising an X-ray source, a detector, a data collecting module and a processor. Said X-ray source is located at a first side of an object to be imaged. Said detector is located at a second side of said object, for receiving an X-ray that is emitted by said X-ray source and passes through said object and generating an output signal of said detector. Said data collecting module is used for collecting said output signal of said detector to generate an input image. Said processor is used for processing said input image. Said processing step comprises: identifying a weak edge comprising a plurality of weak edge pixels and a strong edge comprising a plurality of strong edge pixels in said input image; filtering at least a part of said input image to obtain a smoothed image, during which said weak edge in said input image is filtered with a first filter and said strong edge in said input image is filtered with a second filter having a smoothness less than that of said first filter; acquiring edge information of said input image based on said input image and said smoothed image; and generating an output image based on said edge information and said smoothed image.

BRIEF DESCRIPTION OF THE DRAWINGS

These and other features, aspects and advantages of the present invention can be understood better in light of the following detailed description with reference to the accompanying drawings, in which the same reference signs represent the same components in the whole drawings, in which.

DETAILED DESCRIPTION

In order to help the person skilled in the art to understand the subject matter claimed by the present invention, detailed description of embodiments of the present invention will be given with reference to the accompanying drawings in the detailed description. In the following detailed description of those embodiments, some known functions or structures will not be described in detail, to avoid disclosure of the present invention to be affected by unnecessary details.

Unless defined otherwise, the technical or scientific terms used in the Claims and the Description should have meanings as commonly understood by one of ordinary skilled in the art to which the present disclosure belongs. The terms "first", "second" and the like in the Description and the Claims do not mean any sequential order, quantity or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, but may comprise electric connection, no matter directly or indirectly.

Figure 1:
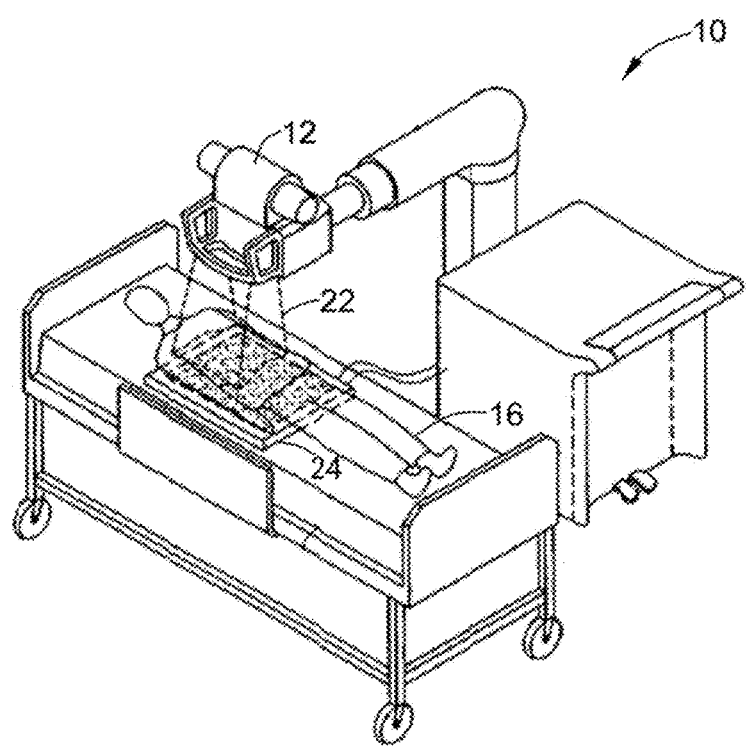
FIG. 1 is a schematic diagram of one embodiment of an imaging system.
Figure 2:
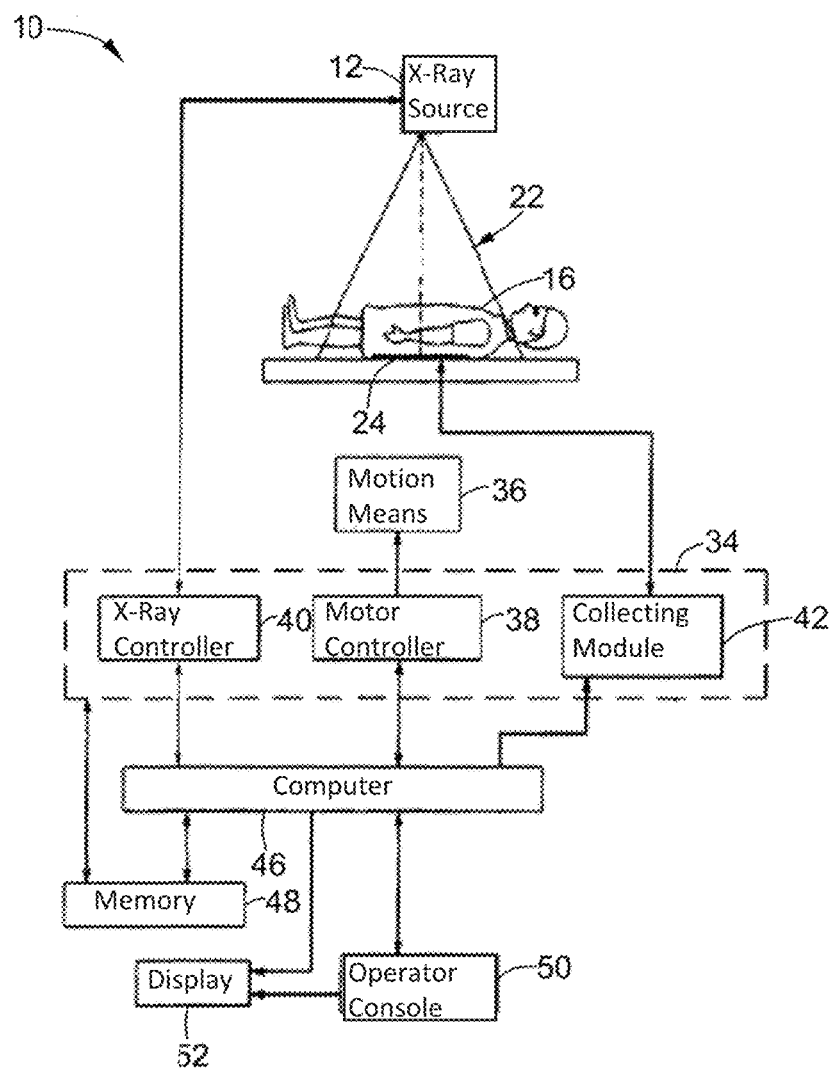
FIG. 2 is a schematic block diagram of the imaging system as shown in FIG. 1.

FIG. 1 is a schematic diagram of an imaging system 10. FIG. 2 is a schematic block diagram of the system 10 as shown in FIG. 1. In an embodiment as shown in FIG. 1, the imaging system 10 is an X-ray imaging system, which includes an X-ray source 12 and a detector 24. The X-ray source 12 is located at a first side of an object (e.g., a patient) 16 to be imaged, for projecting an X-ray beam 22 towards the object 16. The detector 24 is located at a second side of the object 16, for receiving an X-ray that is emitted by said X-ray source 12 and then attenuated by passing through the object 16, and generating an output signal of the detector. Specifically, said detector 24 includes a plurality of detector elements arranged in a two-dimensional (2D) array, which consists of a plurality of detector rows (not shown), each of which includes a plurality of detector elements that are used together for sensing the X-ray passing through the object 16. Each detector element generates an electrical signal that is proportional to an X-ray flux absorbed at a position where it is located.

The X-ray imaging system 10 includes a system controller 34 for controlling and managing operation of the X-ray source 12 and the detector 24. The system controller 34 includes an X-ray controller 40 for supplying energy and a timing signal for said X-ray source 12 and a motor controller 38 for controlling motion means 36. The motion means 36 may cause the X-ray source 12 and the detector 24 to move in one or more directions of space with respect to the object 16. In some embodiments, the motion means 36 may include a supporting structure, e.g., a C-arm.

The system controller 34 further includes a data collecting module 42 for collecting the output signal of the detector 24 from said detector. In some embodiments, the output signal of said detector is an analog signal. The data collecting module 42 converts the analog signal into a digital signal and generates an input image. The system controller 34 further includes a processor (not shown) for processing said input image to generate an output image, which may be installed in a computer 46 or the data collecting module 42.

The X-ray imaging system 10 further includes a display 52 for displaying said input image, said output image and/or other data. The computer 46 also receives an instruction and a scanning parameter inputted by an operator console 50, which includes a keyboard and/or other input means. The computer 46 utilizes the instruction and the parameter provided by an operator to supply a control signal and information to the data collecting module 42, the X-ray controller 40 and the motor controller 38. The X-ray imaging system 10 further includes a memory 48 for storing said input image, said output image and/or other data.

In some embodiments, the processor is programmed with programs for performing steps of the following method. In other embodiments, the computer 46 is programmed with programs for implementing functions as described herein. Hence, the computer as called herein is not limited to a computer represented by a usually-called integrated circuit in the industry, and should have a boarder range, including a computer, a processor, a single-chip computer, a microelectronic meter, a programmable logic controller, an application-specific integrated circuit and other programmable devices. Said processor or computer 46 programmed with the programs may process the image and reduce artifacts in the image, which will be described in details hereinafter. It is noted that the following method is not limited to be used in the X-ray imaging system 10, and may also be used in image processing of other different types of imaging systems, e.g., a tomography machine (CT) imaging system.

One aspect of the embodiments of the present invention relates to an image processing method that can reduce or eliminate artifacts on the output image, especially overshoot or undershoot artifacts due to edge enhancement.

Figure 3:
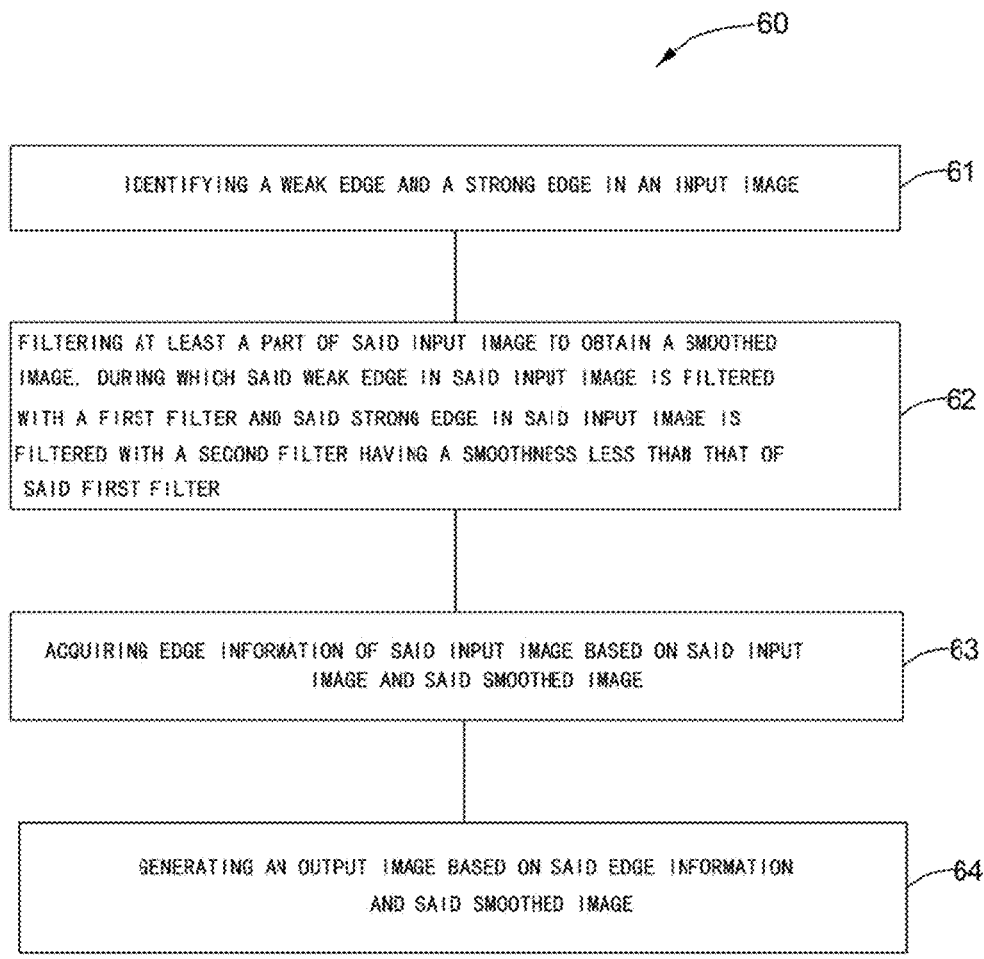
FIG. 3 is a schematic flow chart of an image processing method according to one specific embodiment of the present invention.

FIG. 3 is a schematic flow chart of an image processing method 60 according to one embodiment of the present invention. The method 60 includes an edge identifying step 61, a filtering step 62, an edge information acquiring step 63 and an output image generating step 64.

In Step 61, a weak edge including a plurality of weak edge pixels and a strong edge including a plurality of strong edge pixels in an input image are identified. Specifically, the weak edge pixels and the strong edge pixels in the input image are identified. A so-called strength of an edge refers to a visual difference level between one side and another side of the edge, which may also be characterized by a gray value or a RGB value of a pixel. RGB is a method for coding colors. When this coding method is used, each color may be represented by strengths of red, green and blue. The greater the difference between two sides of the edge is, the stronger the edge is; and the less the difference between two sides of the edge is, the weaker the edge is. Take a tissue of a human body as an example, air (a bubble), a soft tissue or the like usually presents a weaker edge on the image, and a skeleton or metal (a steel nail, a false tooth or the like implanted into the body of a patient) usually presents a stronger edge on the image. In the embodiment of the present invention, the weak edge and the strong edge may be defined and divided by absolute gradient values of pixels in the edge. For example, an edge with pixels whose absolute gradient values are within the range of Lw to Hw is defined as a weak edge, and an edge with pixels whose absolute gradient values are within the range of Ls to Hs is defined as a strong edge.

In Step 62, at least a part of said input image is filtered to obtain a smoothed image. Specifically, the strong edge and the weak edge identified in Step 61 are filtered. The weak edge in said input image is filtered with a first filter, and the strong edge in said input image is filtered with a second filter having a smoothness less than that of said first filter. In the embodiment of the present invention, the strong edge and the weak edge are filtered with filters having different smoothnesses, which reduces the smoothness for filtering the strong edge. Said smoothness may characterize a smoothing effect presented by the image after it is processed by the filter. The greater the smoothness is, the better the smoothing effect is. For example, for a Gaussian filter, the greater a weight of a central pixel of a Gaussian kernel with respect to its surrounding pixels, the less the smoothness. In some embodiments, said step of filtering the image further includes filtering a non-edge part of the input image with said first filter.

Said first filter may include a low pass filter, e.g., a Gaussian filter that employs a Gaussian kernel (kernel$_G$) to perform convolution operation on the image so as to achieve objectives of smoothing the image and removing noise.

Said second filter may employ a constant smoothness less than that of the first filter to filter all the strong edge pixels, and may also employ a different smoothness to filter each strong edge pixel respectively according to a different strength of each strong edge pixel.

In some embodiments, said second filter includes a plurality of subfilters for filtering a plurality of strong edge pixels in said strong edge respectively, and a smoothness of each subfilter is in negative correlation with an absolute gradient value of the corresponding strong edge pixel. Specifically, a filtering function of said second filter is determined based on a filtering function of the first filter and an absolute gradient value of the corresponding strong edge pixel. In the case of the first filter being a Gaussian filter, a kernel operator (kernel$_2$) of the second filter may be determined based on a preset Gaussian kernel (kernel$_G$) of the first filter and an absolute gradient value (t) of the corresponding strong edge pixel, and the kernel operator of said second filter may be calculated by the following formula:

$$\text{kernel}_2 = \text{kernel}_G * \exp(-k*d^2) \quad (1)$$

$$\text{wherein } k = A*[1-(3*\text{smooth\_factor}^2 - 2*\text{smooth\_factor}^3)] \quad (2)$$

$$\text{smooth\_factor} = 1 - \frac{t - L_s}{M} \quad (3)$$

$d^2$ in the formula (1) is a matrix having the same order as the Gaussian kernel (kernel$_G$), which characterizes a distance relationship between the corresponding strong edge pixel (central pixel) and adjacent pixels. Similar to the Gaussian kernel, a central element of the matrix corresponds to a strong edge pixel (a central pixel) to be filtered, and each element value in the matrix is in positive correlation with a distance between it and the central element. In some embodiments:

$$d^2 = \begin{vmatrix} 8 & 5 & 2 & 5 & 8 \\ 5 & 2 & 1 & 2 & 5 \\ 2 & 1 & 0 & 1 & 2 \\ 5 & 2 & 1 & 2 & 5 \\ 8 & 5 & 2 & 5 & 8 \end{vmatrix}.$$

In the formulas (2) and (3), A is an amplification factor for controlling an edge remain strength with regard to the strong edge. smooth_factor is a smoothing factor for determining a smoothness of said subfilter. M is a constant for adjusting a value of smooth_factor according to properties of a system. Ls is a lower limit of a gradient range of the strong edge, $t \geq L_S$. It can be seen from the formula (3) that the smoothing factor smooth_factor is in linearly negative correlation with an absolute gradient value t of the corresponding strong edge pixel.

In Step 63, edge information of said input image is acquired based on said input image and said smoothed image. In some embodiments, said step of acquiring edge information includes subtracting said smoothed image from said input image to obtain a difference image, which contains said edge information. This is because a difference between a non-edge part of the smoothed image and the corresponding part of the input image is less and a difference between strong edge and weak edge parts and the corresponding part of the input image is greater. When the smoothed image is subtracted from the input image, the non-edge part is offset and the edge parts are extracted separately from said difference image, and the greater the smoothness of edge filtering, the more an information extraction amount. Since the strong edge is filtered with a less smoothness in Step 62, the extraction amount of strong edge information is less in Step 63, which can ensure that the strong edge will not be over-enhanced so as to result in overshoot and undershoot artifacts.

In Step 64, an output image is generated based on said edge information and said smoothed image. Specifically, said step of generating an output image includes multiplying said difference image with a scale factor to obtain an enhanced difference image. An objective of this step is to enhance said edge information such that the edge becomes sharper. A degree of edge enhancement may be controlled by adjusting said scale factor. Then, said enhanced difference image and said smoothed image are added so as to generate said output image.

In addition to the weak edge and the strong edge, there may also be an ultra-strong edge having a strength higher than that of the strong edge in the input image. Like the strong edge, presence of the ultra-strong edge will also results in artifacts, which affects imaging quality. In some embodiments, the ultra-strong edge may be not filtered. As such, after the smoothed image is subtracted from the input image, the ultra-strong edge will be completely offset, will not be acquired, and thus will also not be enhanced and in turn resulting in artifacts.

Figure 4:
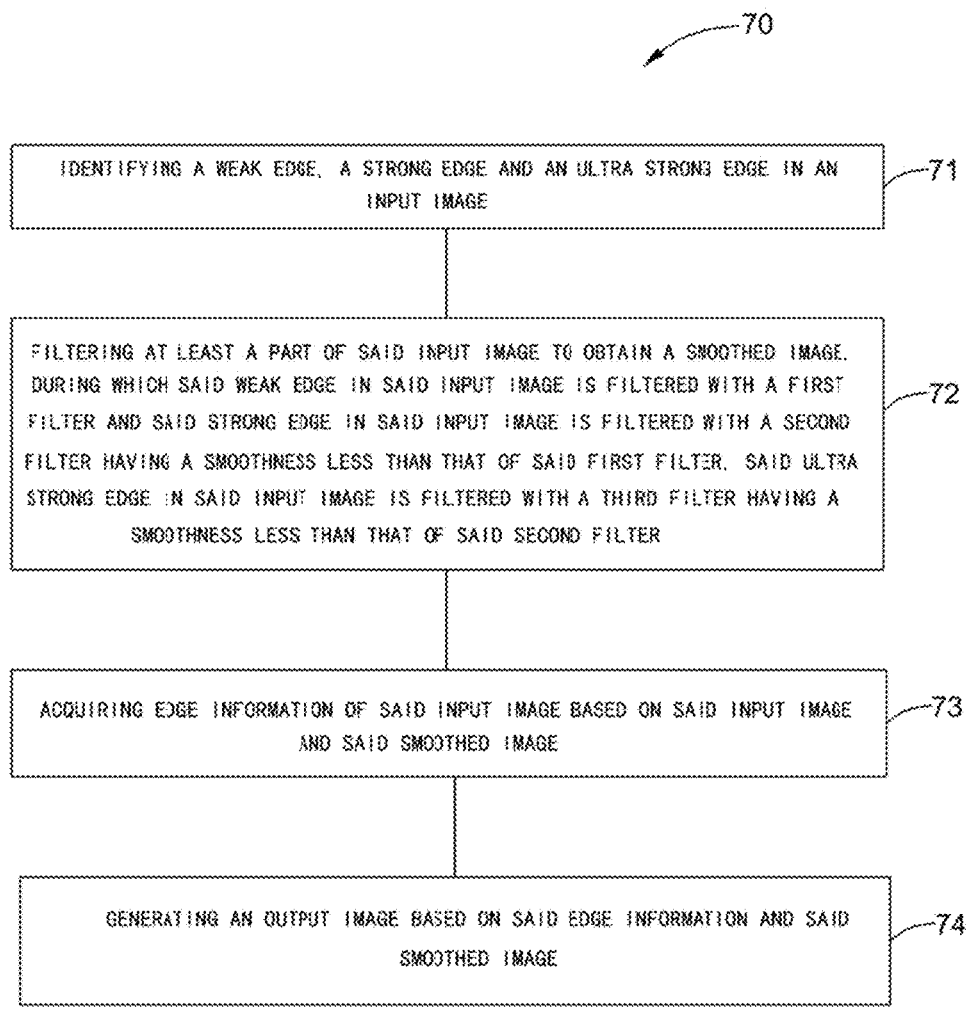
FIG. 4 is a schematic flow chart of an image processing method according to another specific embodiment of the present invention.

In other embodiments, the ultra-strong edge may be filtered with an extremely low smoothness to reduce the information extraction amount of the ultra-strong edge as much as possible. With reference to FIG. 4, FIG. 4 is a schematic flow chart of an image processing method 70 according to another embodiment of the present invention. The method 70 includes an edge identifying step 71, a filtering step 72, an edge information acquiring step 73 and an output image generating step 74, which are similar to Step 61, Step 62, Step 63 and Step 64 in the method 60 respectively.

Unlike the method 60, in Step 71, in addition to identifying a weak edge and a strong edge in an input image, an ultra-strong edge in the input image is also identified. Accordingly, in Step 72, in addition to filtering said strong edge and said weak edge, the ultra-strong edge identified in Step 71 is also filtered with a third filter. A smoothness of said third filter is less than that of said second filter. When said second filter includes a plurality of subfilters, the smoothness of said third filter is less than a minimum value among smoothnesses of said plurality of subfilters. A kernel operator (kernel$_3$) of said third filter may be calculated by the following formula:

$$\text{kernel}_3 = \text{kernel}_G * \exp(-A*d^2)$$

Wherein kernel$_G$ is a Gaussian kernel of the first filter, and $d^2$ characterizes a distance relationship between the corresponding ultra-strong edge pixel (central pixel) and adjacent pixels. In some embodiment, $$d^2 = \begin{vmatrix} 8 & 5 & 2 & 5 & 8 \\ 5 & 2 & 1 & 2 & 5 \\ 2 & 1 & 0 & 1 & 2 \\ 5 & 2 & 1 & 2 & 5 \\ 8 & 5 & 2 & 5 & 8 \end{vmatrix}.$$

A is an amplification factor for controlling an edge remain strength with regard to the ultra-strong edge.

Both Step 61 and Step 71 as described above relate to the step of identifying an edge type. Since an edge in an image is constituted of pixels, the key to identifying the edge and the edge type is to judge and classify each pixel. In the image, since an absolute gradient value of an edge pixel is generally much higher than that of a non-edge pixel, an absolute gradient value of an ultra-strong edge pixel is higher than that of a strong edge pixel, and the absolute gradient value of the strong edge pixel is higher than that of a weak edge pixel, it may be judged whether the pixel is an edge pixel by an absolute gradient value of each pixel, in turn it is further judged whether the pixel is a weak edge pixel, a strong edge pixel or an ultra-strong edge pixel. "The absolute gradient value" as described herein characterizes a variation ratio of a pixel value of one pixel with respect to its adjacent pixels, in which "the adjacent pixels" refer to pixels that are adjacent to the pixel, which may be four pixels above, below, to the left and to the right of the pixel and may also be eight pixels above, below, to the left, to the right, to the upper left, to the lower left, to the upper right and to the lower right of the pixel, and "the pixel value" refers to a gray value of the pixel or a RGB value of the pixel.

Figure 5:
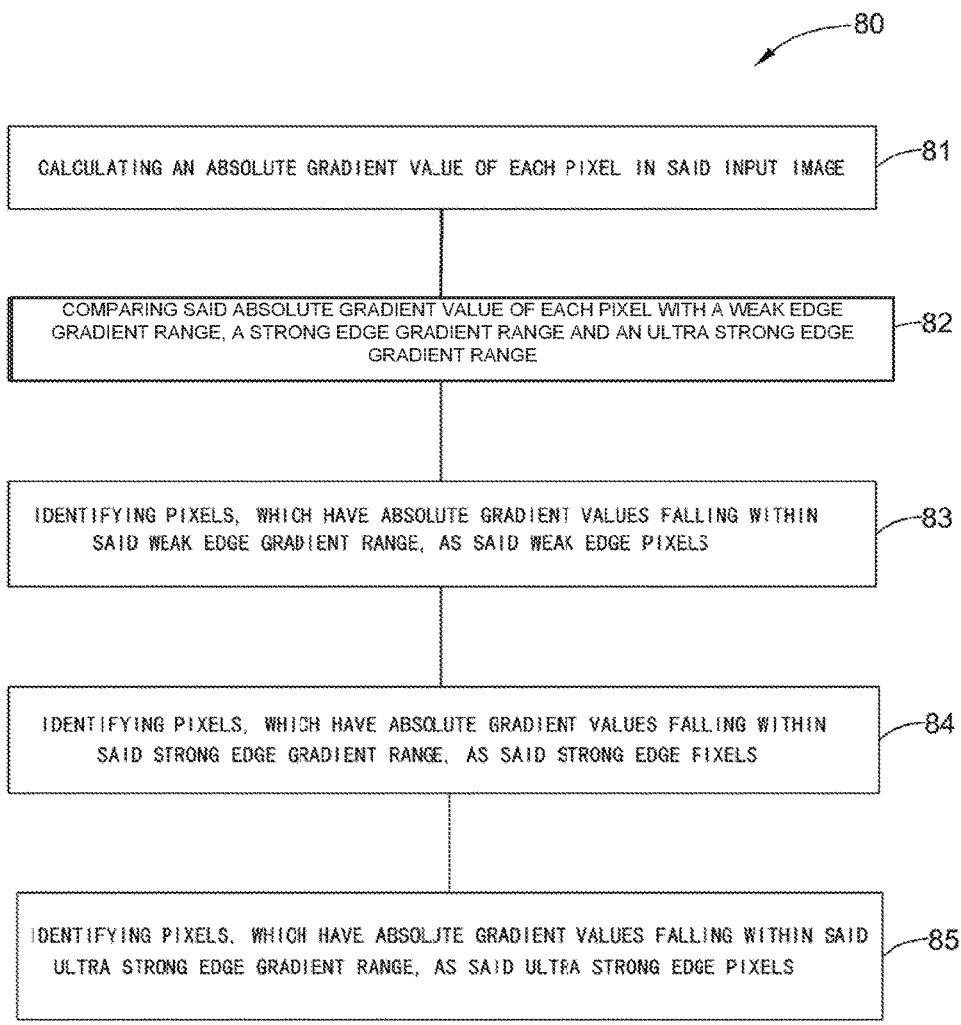
FIG. 5 is a schematic flow chart of an edge identifying step according to one specific embodiment of the present invention.

With reference to FIG. 5, FIG. 5 is a schematic flow chart of an edge type identifying step 80 according to one embodiment of the present invention.

In Step 81, an absolute gradient value of each pixel in said input image is calculated. Said absolute gradient value is calculated based on a plurality of pixel differences between the pixel and a plurality of adjacent pixels. Said absolute gradient value may be a maximum value of said plurality of pixel differences, and may also be an average value or a median value of said plurality of pixel differences. In some embodiments, an absolute gradient value (t) of a target pixel is calculated according to the following formula:

$$t = F(x(i,j), Fy(i,j))$$

Wherein (i,j) is a coordinate of the target pixel, $Fx(i,j)$ is a gradient value of the pixel in the X direction, $Fy(i,j)$ is a gradient value of the pixel in the Y direction, and an absolute gradient value of the pixel is a greater one between them.

In Step 82, said absolute gradient value of each pixel is compared with a weak edge gradient range, a strong edge gradient range and an ultra-strong edge gradient range. Said weak edge gradient range, said strong edge gradient range and said ultra-strong edge gradient range may be estimated comprehensively according to factors such as a type of an imaging system, imaging quality or the like. In some embodiments, said weak edge gradient range, and said strong edge gradient range may be calculated based on a noise amplitude of said input image.

In Step 83, pixels, which have absolute gradient values falling within said weak edge gradient range, are identified as said weak edge pixels. In Step 84, pixels, which have absolute gradient values falling within said strong edge gradient range, are identified as said strong edge pixels. In Step 85, pixels, which have absolute gradient values falling within said ultra-strong edge gradient range, are identified as said ultra-strong edge pixels.

Figure 6:
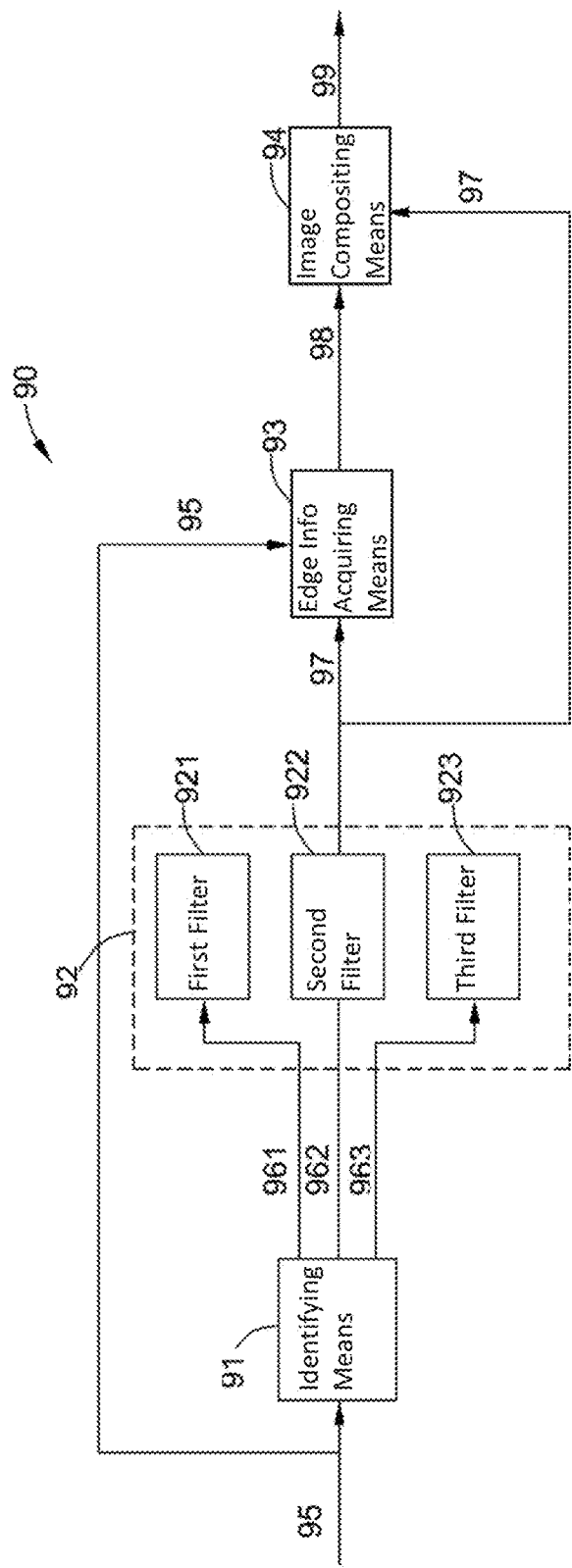
FIG. 6 is a schematic diagram of an image processing system according to one specific embodiment of the present invention.

An embodiment of the present invention also relates to an image processing system 90, as shown in FIG. 6. With reference to FIG. 6, said image processing system 90 includes an edge identifying means 91, a filter 92, an edge information acquiring means 93 and an image compositing means 94. The edge identifying means 91 is used for identifying a weak edge 961 including a plurality of weak edge pixels and a strong edge 962 including a plurality of strong edge pixels in an input image 95. The filter 92 is used for filtering at least a part of the input image 95 to obtain a smoothed image 97. The filter 92 includes a first filter 921 and a second filter 922, in which the first filter 921 is used for filtering the weak edge 961 in said input image and the second filter 922 is used for filtering the strong edge 962 in said input image. Wherein a smoothness of the second filter 922 is less than that of the first filter 921. The edge information acquiring means 93 is used for acquiring edge information 98 of the input image based on the input image 95 and the smoothed image 97. The image compositing means 94 is used for generating an output image 99 based on the edge information 98 and the smoothed image 97.

In some embodiments, the edge identifying means 91 is also used for identifying an ultra-strong edge 963 including a plurality of ultra-strong edge pixels in the input image. Accordingly, the filter 92 further includes a third filter 923 for filtering the ultra-strong edge 963 in the input image, which has a smoothness less than that of the second filter 922.

Figure 8:
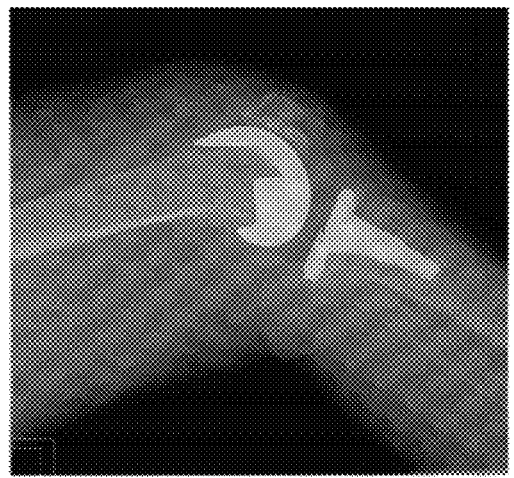
FIG. 8 is an output image obtained after an input image is processed by the image processing method as described in the embodiments of the present invention.
Figure 7:
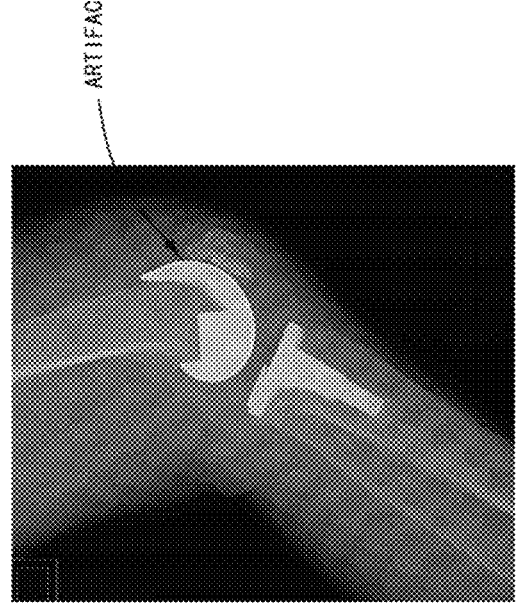
FIG. 7 is an output image obtained after a Gaussian filter filters the entire input image on which edge enhancement is then performed.

The image processing method as described in the embodiments of the present invention can reduce or eliminate artifacts on the output image. FIG. 7 and FIG. 8 show a set of comparative examples. In FIG. 7, the entire input image is filtered with a Gaussian filter and then edge enhancement is performed on the input image to obtain an output image. It can be observed that obvious artifacts exist in FIG. 7. This is because the same filter is used for the strong edge and the weak edge, which causes the strong edge to be over-enhanced. FIG. 8 is an output image obtained after the input image is processed by the method as described in the embodiments of the present invention. It can be observed that artifacts at the corresponding position in FIG. 7 is eliminated. As such, more details around the edge are presented, which facilitates a doctor to make more accurate diagnosis. The present embodiment manifests that the image processing method as disclosed by the present invention can effectively inhibit or eliminate artifacts in an X-ray image so as to improve imaging quality.

Although the present invention has been set forth in details in combination with specific embodiments, the person skilled in the art shall be understood that many modifications and variations may be made to the present invention. Therefore, it should be recognized that the intention of the claims is to cover all these modifications and variations within the real concept and range of the present invention.

What is claimed is:

1. An image processing method comprising:
   identifying a weak edge comprising a plurality of weak edge pixels and a strong edge comprising a plurality of strong edge pixels in an input image, said identifying step comprising calculating an absolute gradient value of each pixel in said input image, comparing said absolute gradient value of each pixel with a weak edge gradient range and a strong edge gradient range, identifying said weak edge pixels as pixels having absolute gradient values falling within said weak edge gradient range, and identifying said strong edge pixels as pixels having absolute gradient values falling within said strong edge gradient range;
   filtering at least a part of said input image to obtain a smoothed image, during which said weak edge in said input image is filtered with a first filter and said strong edge in said input image is filtered with a second filter having a smoothness less than that of said first filter;
   acquiring edge information of said input image based on said input image and said smoothed image; and
   generating an output image based on said edge information and said smoothed image.

2. The method according to claim 1, wherein said absolute gradient value is calculated based on a plurality of pixel value differences between said pixel and a plurality of adjacent pixels, and said absolute gradient value comprises a maximum, an average or a median among said pixel value differences.

3. An image processing method comprising:
- identifying a weak edge comprising a plurality of weak edge pixels and a strong edge comprising a plurality of strong edge pixels in an input image;
- filtering at least a part of said input image to obtain a smoothed image, during which said weak edge in said input image is filtered with a first filter and said strong edge in said input image is filtered with a second filter having a smoothness less than that of said first filter;
- acquiring edge information of said input image based on said input image and said smoothed image; and
- generating an output image based on said edge information and said smoothed image, wherein said second filter comprises a plurality of subfilters for filtering said plurality of strong edge pixels of said strong edge respectively, and a smoothness of each subfilter is in negative correlation with an absolute gradient value of the corresponding strong edge pixel.

4. The method according to claim 3, wherein said first filter comprises a low pass filter.

5. The method according to claim 3, wherein the first filter is a Gaussian filter.

6. An image processing method comprising:
- identifying a weak edge comprising a plurality of weak edge pixels and a strong edge comprising a plurality of strong edge pixels in an input image;
- filtering at least a part of said input image to obtain a smoothed image, during which said weak edge in said input image is filtered with a first filter and said strong edge in said input image is filtered with a second filter having a smoothness less than that of said first filter;
- acquiring edge information of said input image based on said input image and said smoothed image;
- identifying an ultra-strong edge comprising a plurality of ultra-strong edge pixels in said input image, during which said ultra-strong edge is filtered with a third filter having a smoothness less than that of said second filter; and
- generating an output image based on said edge information and said smoothed image.

7. An image processing method comprising:
- identifying a weak edge comprising a plurality of weak edge pixels and a strong edge comprising a plurality of strong edge pixels in an input image;
- filtering at least a part of said input image to obtain a smoothed image, during which said weak edge in said input image is filtered with a first filter and said strong edge in said input image is filtered with a second filter having a smoothness less than that of said first filter;
- acquiring edge information of said input image based on said input image and said smoothed image, said acquiring step comprising subtracting said smoothed image from said input image to obtain a difference image; and
- generating an output image based on said edge information and said smoothed image, said generating step comprising multiplying said difference image with a scale factor to obtain an enhanced difference image and adding said enhanced difference image to said smoothed image.

8. An image processing apparatus comprising:
- an edge identifying means for identifying a weak edge comprising a plurality of weak edge pixels and a strong edge comprising a plurality of strong edge pixels in an input image;
- a filter for filtering at least a part of said input image to obtain a smoothed image, said filter comprising:
  - a first filter for filtering said weak edge in said input image; and
  - a second filter for filtering said strong edge in said input image, said second filter comprising a plurality of subfilters for filtering said plurality of strong edge pixels of said strong edge respectively, and a smoothness of each subfilter is in negative correlation with an absolute gradient value of the corresponding strong edge pixel;
- an edge information acquiring means for acquiring edge information of said input image based on said input image and said smoothed image; and
- an image compositing means for generating an output image based on said edge information and said smoothed image.

9. An imaging system comprising:
- an X-ray source located at a first side of an object to be imaged;
- a detector located at a second side of said object to be imaged to receive an X-ray emitted by said X-ray source that passes through said object to be imaged and generate an output signal;
- a data collecting module for collecting said output signal of said detector to generate an input image; and
- the image processing apparatus of claim 8 to process said input image.

10. The image processing apparatus of claim 8, wherein a smoothness of said second filter is less than that of said first filter.

* * * * *